(12) United States Patent
Johnson et al.

(10) Patent No.: US 10,186,006 B2
(45) Date of Patent: Jan. 22, 2019

(54) INTERFACE FEED ANALYZER FOR CODE MAPPING

(71) Applicant: General Electric Company, Schenectady, NY (US)

(72) Inventors: Cessily Johnson, Salt Lake City, UT (US); Douglas Irwin, Murray, UT (US)

(73) Assignees: General Electric Company, Schenectady, NY (US); IHC HEALTH SERVICES, INC, Salt Lake City, UT (US)

( * ) Notice: Subject to any disclaimer, the term of this patent is extended or adjusted under 35 U.S.C. 154(b) by 1211 days.

(21) Appl. No.: 13/663,900

(22) Filed: Oct. 30, 2012

(65) Prior Publication Data

US 2013/0297328 A1   Nov. 7, 2013

Related U.S. Application Data

(60) Provisional application No. 61/553,771, filed on Oct. 31, 2011.

(51) Int. Cl.
*G06Q 50/22* (2018.01)
*G06Q 10/06* (2012.01)
(Continued)

(52) U.S. Cl.
CPC ............ *G06Q 50/22* (2013.01); *G06F 19/00* (2013.01); *G06Q 10/06* (2013.01); *G06Q 10/10* (2013.01)

(58) Field of Classification Search
CPC ........ G06Q 50/22; G16H 10/00; G16H 10/20; G16H 10/40; G16H 10/60; G16H 10/65; G16H 15/00; G16H 20/00; G16H 20/10; G16H 20/13; G16H 20/17; G16H 20/30; G16H 20/40; G16H 20/60; G16H 20/70; G16H 20/90; G16H 30/00; G16H 40/00; G16H 40/20; G16H 40/40; G16H 40/60; G16H 40/63; G16H 40/67; G16H 50/00; G16H 70/00; G16H 70/20; G16H 70/40; G16H 70/60; G16H 80/00
See application file for complete search history.

(56) References Cited

U.S. PATENT DOCUMENTS

| 2006/0064328 | A1* | 3/2006 | Datta | ................ G06F 17/227 705/3 |
| 2007/0118540 | A1* | 5/2007 | Guo | ................ G06F 17/30265 |
| 2010/0008553 | A1 | 1/2010 | Holstrom | |

* cited by examiner

*Primary Examiner* — Linh Giang Le
(74) *Attorney, Agent, or Firm* — Hanley, Flight and Zimmerman, LLC

(57) ABSTRACT

Certain examples provide systems, methods, and apparatus to provide clinical terminology services. Certain examples provide systems, methods, and apparatus to analyze and map a new interface message feed. An example clinical interface feed analysis system includes an interface analyzer to: receive a clinical message feed including content; automatically compare the content from the clinical message feed to a reference to match and map the content to at least one of reference clinical data and coded terminology included in the reference without user input; and provide a proposed interface output for review. The example system includes a tester to facilitate testing of the proposed interface output in conjunction with a clinical system to release the proposed interface output as an interface for incoming messages. The example system is to update the reference based on the content from the clinical message feed and the interface mapping.

17 Claims, 8 Drawing Sheets

(51) Int. Cl.
*G06Q 10/10* (2012.01)
*G06F 19/00* (2018.01)

INTERFACE FEED ANALYZER FOR CODE MAPPING

CROSS-REFERENCE TO RELATED APPLICATIONS

This patent claims priority to U.S. Provisional Application Ser. No. 61/553,771, entitled "Interface Feed Analyzer for Code Mapping," which was filed on Oct. 31, 2011, and is hereby incorporated herein by reference in its entirety.

FIELD

The present invention generally relates to healthcare terminology mapping. In particular, the present invention relates to systems, methods, and apparatus for matching concepts between one code scheme and another.

BACKGROUND

Medical terminology is voluminous, fragmented, and complex. Multiple standards bodies (e.g., Health Level Seven (HL7), World Health Organization (WHO), etc.) make contributions to categorizing and publishing medical vocabularies (e.g. Systematized Nomenclature of Medicine (SNOMED), International Classification of Diseases (ICD), Logical Observation Identifier Names and Codes (LOINC), etc.) across multiple healthcare domains (e.g., medical procedures, problem lists, laboratory, etc.).

Most approaches to managing terminologies rely on mapping rules and use of human intervention of terminology engineers or medical coders to understand differences across source vocabularies, to rationalize the organization of data (via hierarchies and relationships), to identify differences in granularity, and to map between codes and synonyms where there is overlap. This process requires a large amount of manpower to maintain an updated vocabulary and is especially burdensome when implementing new systems in an established healthcare organization with an abundance of systems and proprietary codes and synonyms. Combined with internationalization and a desire to share data across healthcare organizations, the problem quickly becomes unmanageable. For this reason, many healthcare IT providers have created their own proprietary codes, relationships, terms, and picklists which remain unintegrated with other systems and terminologies. Otherwise, the human effort involved can occupy a team of humans for months to find matches between terminologies.

BRIEF SUMMARY

Certain examples provide systems, methods, and apparatus to provide clinical terminology services. Certain examples provide systems, methods, and apparatus to analyze and map a new interface message feed.

Certain examples provide a computer-implemented method of mapping a clinical interface message feed to reference clinical data and coded terminology. The example method includes receiving, at an interface analyzer, a clinical message feed including content; automatically comparing the content from the clinical message feed to a reference to match and map the content to at least one of reference clinical data and coded terminology without user input; providing a proposed interface output for review via the interface analyzer; facilitating testing, via the interface analyzer, of the proposed interface output in conjunction with a clinical system; releasing the proposed interface output as an interface for incoming messages at a clinical system; and updating the reference based on the content from the clinical message feed.

Certain examples provide a clinical interface feed analysis system. The example system includes an interface analyzer to: receive a clinical message feed including content; compare the content from the clinical message feed to a reference to match and map the content to at least one of reference clinical data and coded terminology without user input; and provide a proposed interface output for review. The example system includes a tester to facilitate testing of the proposed interface output in conjunction with a clinical system to release the proposed interface output as an interface mapping for incoming messages. The example system is to update the reference based on the content from the clinical message feed.

Certain examples provide a tangible computer readable storage medium including executable program instructions which, when executed by a computer processor, cause the computer to implement a clinical interface feed analysis system. The example system includes an interface analyzer to: receive a clinical message feed including content; compare the content from the clinical message feed to a reference to match and map the content to at least one of reference clinical data and coded terminology; and provide a proposed interface output for review. The example system includes a tester to facilitate testing of the proposed interface output in conjunction with a clinical system to release the proposed interface output as an interface mapping for incoming messages. The example system is to update the reference based on the content from the clinical message feed.

Figure 1:
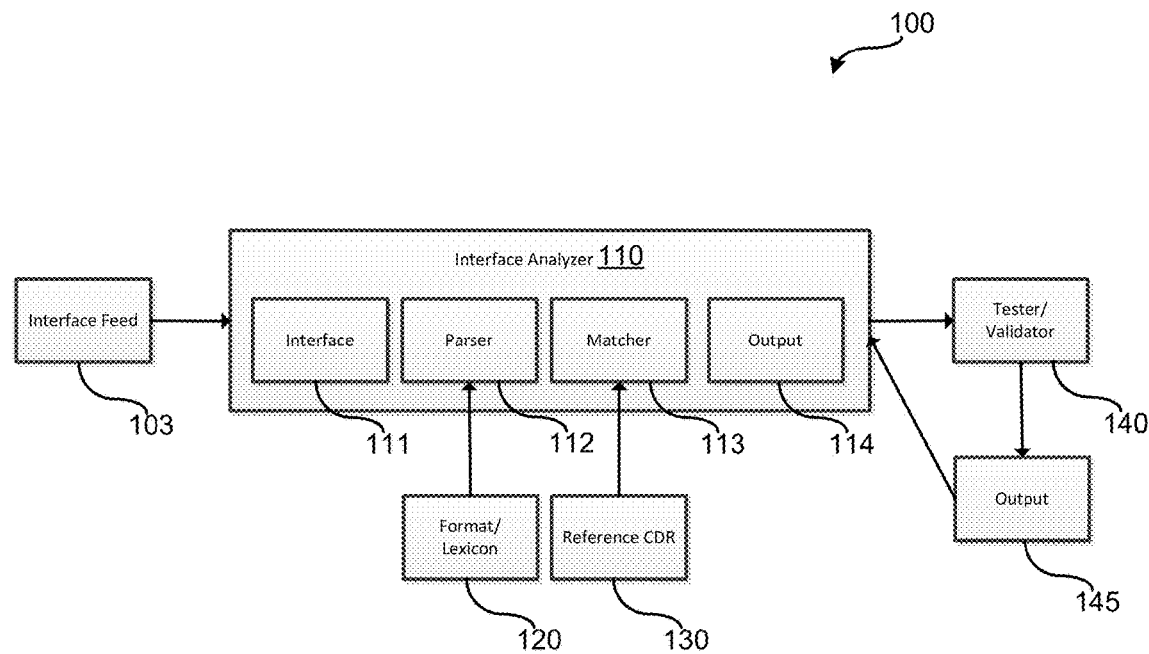
FIG. 1 illustrates an example interface feed analysis system to analyze, test, and enable implementation of a clinical interface.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF CERTAIN EXAMPLES

Although the following discloses example methods, systems, articles of manufacture, and apparatus including, among other components, software executed on hardware, it should be noted that such methods and apparatus are merely illustrative and should not be considered as limiting. For example, it is contemplated that any or all of these hardware and software components could be embodied exclusively in hardware, exclusively in software, exclusively in firmware, or in any combination of hardware, software, and/or firmware. Accordingly, while the following describes example methods, systems, articles of manufacture, and apparatus, the examples provided are not the only way to implement such methods, systems, articles of manufacture, and apparatus.

When any of the appended claims are read to cover a purely software and/or firmware implementation, in an embodiment, at least one of the elements is hereby expressly defined to include a tangible medium such as a memory, DVD, CD, Blu-ray, etc., storing the software and/or firmware.

Certain examples provide a tool for comparison and analysis of a new clinical interface feed, such as a Health Level Seven (HL7) interface feed. The tool can be used, for example, to rapidly code clinical data in order to implement and test a new interface quickly. The tool parses the new content and runs matching algorithms with coded terminology and clinical data in order to produce proposed mapping outputs.

Certain examples allow a user to, without manual mapping, compare content from a new interface feed (e.g., an HL7 interface feed) to existing reference clinical data and coded terminology. For example, reference clinical data is stored clinical data (e.g., clinical data stored in a clinical data repository) that has been coded and mapped to a terminology and can be used for an automated mapping of a new interface message feed using the tool. The tool then takes the comparisons and provides outputs that are reviewed before being loaded into the system. Once loaded, the new clinical interface can be implemented for early testing. Additionally, each time this approach is taken and new clinical feeds are mapped to the standard core, the clinical data can be added to the reference repository. Output continues to improve over time and increase the robustness of the reference repository, for example.

For example, when turning on a new clinical interface, mapping of codes passed through the interface is done to properly store the data in a clinical data repository (CDR). The data is stored as coded clinical data and is therefore mapped to a terminology (e.g., a GE Qualibria™ terminology). When conducted manually, this mapping process involves a substantial amount of work, and automated help is useful. Certain examples provide systems and methods for automated assistance with mapping of clinical content.

A technical advantage to this approach to mapping includes early testability of a new clinical interface. Early testability allows a user to rapidly configure and map a large portion of content from a new interface and turn on or activate the interface to begin testing and continue with implementation, for example.

A commercial advantage includes an ability to decrease a time to implement a product, thus decreasing overall implementation costs to provide a competitive advantage.

Certain examples incorporate a reference CDR containing (e.g., previously stored) clinical data that can be compared in different ways as an input to assist text matching tools to map new content to some target. The CDR helps increase accuracy of mapping while reducing false positives, for example. Certain examples allow a more informed comparison of two data sets. New information includes data type comparisons as well as quantitative analysis of values to determine if the values are in an expected range, for example.

Certain examples support coding and structuring of clinical data and comparison to existing clinical data. Alternatively or in addition, certain examples employ matching algorithms and/or facilitate manual review of related clinical data.

As demonstrated by the Health Insurance Portability and Accountability Act (HIPAA), even when the government mandates all entities use a single standard (e.g. X12), standards continually evolve and present customers with an ongoing maintenance cost. This problem has received little attention from the research community, probably because they maintain their own terminologies as part of their research. Universities, for example, have the resources to integrate and maintain references and mappings. Research on ontologies and advanced decision support and natural language processing regularly presupposes harmonized terminologies.

A clinical system that is driven by standardized, coded data can help advance analytics, real-time decision support, and business intelligence for healthcare practitioners.

To aid a human user in terminology mapping (e.g., confirming a computer-generated match of terms), a graphical indication of what is "known" as well as what is "not known" can be provided. For example, an analyzer can be provided which recognizes both "positive space" (e.g., known or likely matches) and "negative space" (e.g., uncertain matches or crowded sets of terms).

An ontology is a representation of information as a set of concepts within a domain, along with relationships between the concepts. An ontology provides a shared vocabulary that can be used to model a domain. Ontologies and associated metadata provide both challenge and opportunity. A web ontology language (OWL) is a family of knowledge representation languages for authoring ontologies. Data described by an ontology in the OWL family is interpreted as a set of "individuals" and a set of "property assertions" that relate these individuals to each other. An ontology includes a set of axioms that place constraints on sets of individuals (called "classes") and type(s) of relationships permitted between the classes. The axioms provide semantics by allowing systems to infer additional information based on the data explicitly provided.

OWL is built on an eXtensible Markup Language (XML) and a resource description framework (RDF), for example. The RDF is a family of World Wide Web Consortium (W3C) specifications designed as a metadata data model. The RDF can be used for conceptual description and/or modeling of web resource information using a variety of syntax formats. Ontologies represented by OWL can be specialized by use (e.g., SNOMED CT), for example. Using OWL, a local ontology can be merged with a global ontology, for example.

FIG. 1 illustrates an example interface feed analysis system 100 to analyze, test, and enable implementation of a clinical interface. The system 100 includes an interface analyzer 110 accepting an interface feed 103 to provide an interface output to a tester/validator 140 using a format/lexicon 120 and a reference CDR 130, for example. The interface analyzer 110 includes an interface 111, a parser 112, a matcher 113, and an output 114, for example.

In operation, an interface feed 103 (e.g., an HL7 clinical interface feed) is provided to the interface analyzer 110 for testing. The interface 111 receives the interface feed 103 and provides the feed 103 to the parser 112. The parser 112 parses the received content according to the format/lexicon 120. The parser 112 provides the parsed content to the matcher 113. The matcher 113 utilizes the reference CDR 130 to run one or more matching algorithms to match the parsed content with coded terminology and clinical data. The matcher 113 provides the matched coded terminology and clinical data to the output 114. The output 114 provides a proposed clinical interface mapping to the tester/validator 140 for testing based on the coded terminology and clinical data. The clinical interface output can be tested and stored, for example, via the tester/validator 140. In certain examples, feedback from the testing can be provided to a user for manual review and revision, automatically tested to monitor for errors, fed back into the interface tester 110 for modification, etc. After the proposed interface has been tested and validated, the clinical interface can be output 145 for use with a clinical system, for example.

Figure 2:
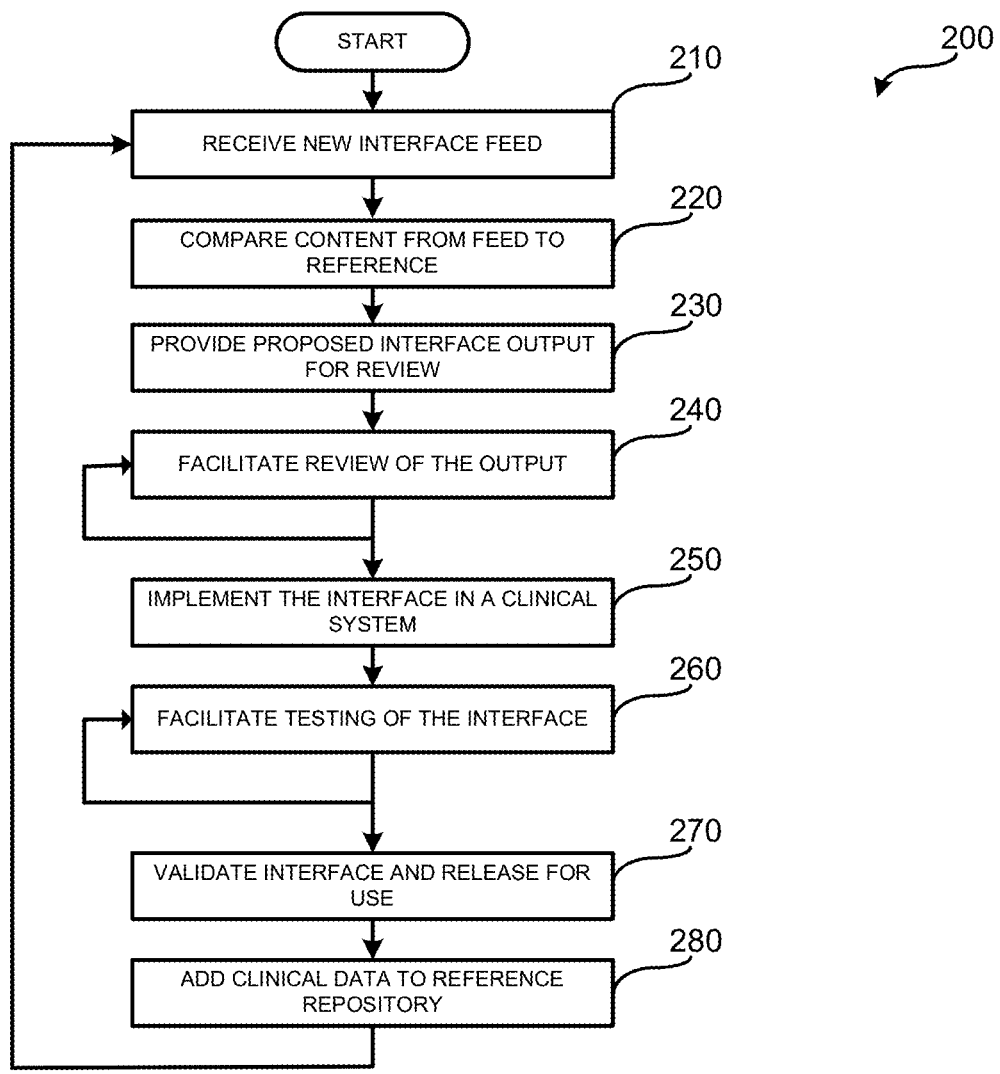
FIG. 2 illustrates a flow diagram for an example method for clinical interface message feed analysis.
Figure 3:
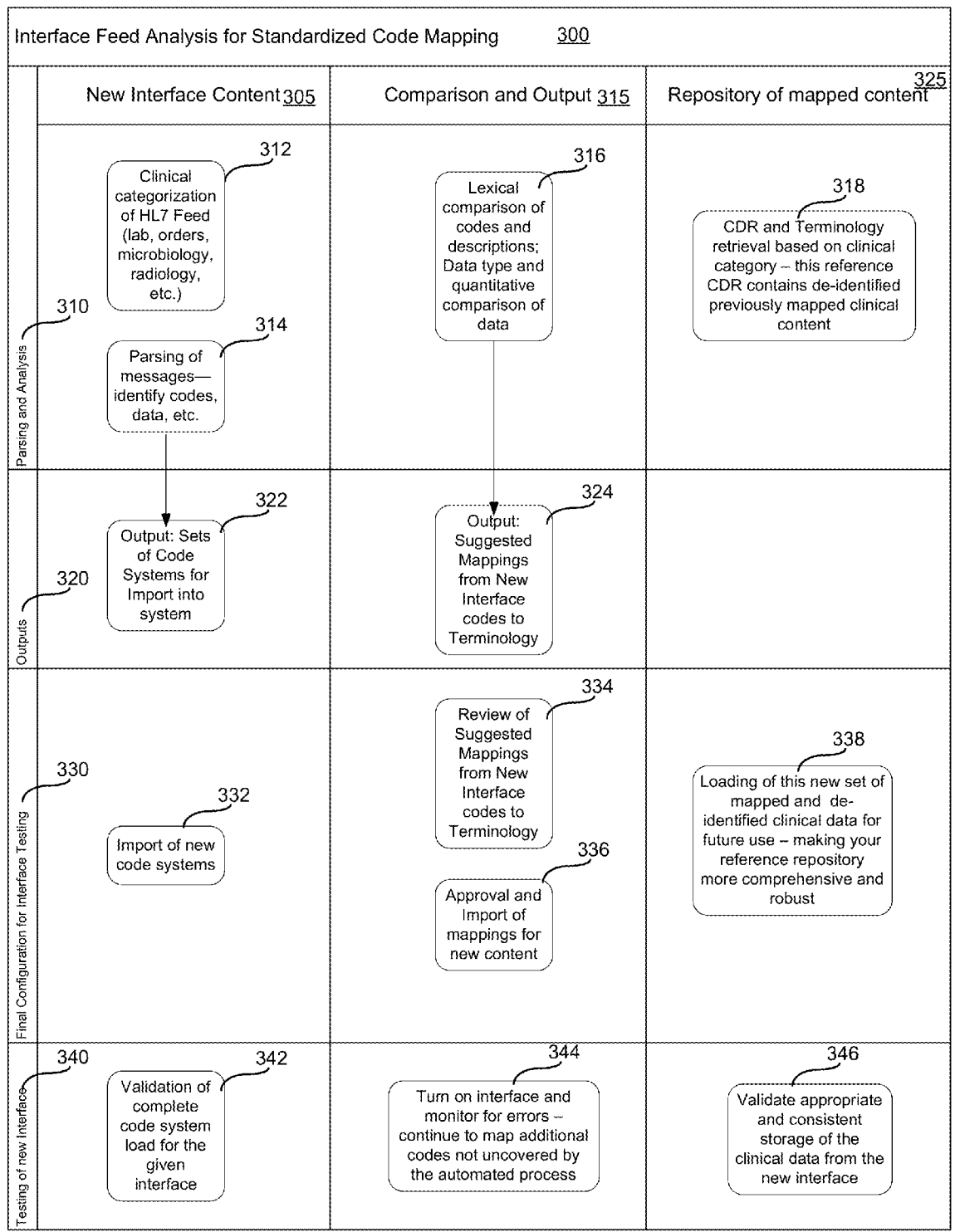
FIG. 3 illustrates a flow diagram of an example automated mapping process to enable implementation of a new clinical interface.
Figure 4:
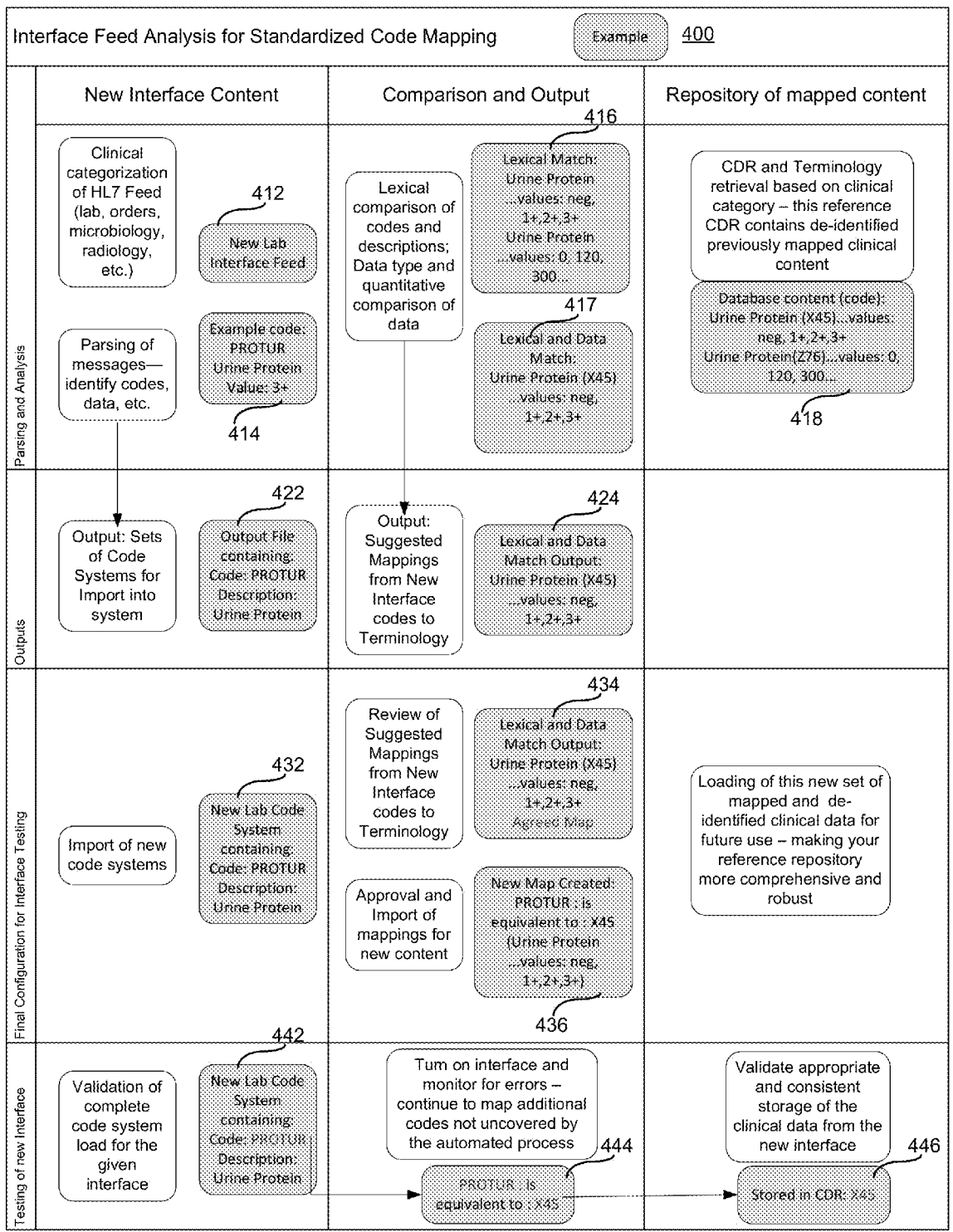
FIG. 4 illustrates a flow diagram of an example automated mapping process to enable implementation of a new clinical interface, applying the process of FIG. 3 to a new laboratory interface feed.

FIGS. 2-4 are flow diagrams representative of example machine readable instructions that can be executed to implement the example systems and/or portions of one or more of those systems described herein. The example processes of FIGS. 2-4 can be performed using a processor, a controller and/or any other suitable processing device. For example, the example processes of FIGS. 2-4 can be implemented using coded instructions (e.g., computer readable instructions) stored on a tangible computer readable medium such as a flash memory, a read-only memory (ROM), and/or a random-access memory (RAM). As used herein, the term tangible computer readable medium is expressly defined to include any type of computer readable storage and to exclude propagating signals. Additionally or alternatively, the example processes of FIGS. 2-4 can be implemented using coded instructions (e.g., computer readable instructions) stored on a non-transitory computer readable medium such as a flash memory, a read-only memory (ROM), a random-access memory (RAM), a cache, or any other storage media in which information is stored for any duration (e.g., for extended time periods, permanently, brief instances, for temporarily buffering, and/or for caching of the information). As used herein, the term non-transitory computer readable medium is expressly defined to include any type of computer readable medium and to exclude propagating signals.

Alternatively, some or all of the example processes of FIGS. 2-4 can be implemented using any combination(s) of application specific integrated circuit(s) (ASIC(s)), programmable logic device(s) (PLD(s)), field programmable logic device(s) (FPLD(s)), discrete logic, hardware, firmware, etc. Also, some or all of the example processes of FIGS. 2-4 can be implemented manually or as any combination(s) of any of the foregoing techniques, for example, any combination of firmware, software, discrete logic and/or hardware. Further, although the example processes of FIGS. 2-4 are described with reference to the flow diagrams of FIGS. 2-4, other methods of implementing the processes of FIGS. 2-4 can be employed. For example, the order of execution of the blocks can be changed, and/or some of the blocks described can be changed, eliminated, sub-divided, or combined. Additionally, any or all of the example processes of FIGS. 2-4 can be performed sequentially and/or in parallel by, for example, separate processing threads, processors, devices, discrete logic, circuits, etc.

FIG. 2 illustrates a flow diagram for an example method 200 for clinical interface message feed analysis. At block 210, a new interface feed is received. For example, a new clinical device message stream is received at a clinical information system. At block 220, content from the feed is compared to reference clinical data (e.g., previously mapped, stored clinical data) and coded terminology that has been previously analyzed and stored. For example, reference clinical data and coded terminology can be stored in a reference repository, vocabulary, and/or lexicon. Such stored content can be used to categorize, parse, and compare the feed, for example.

At block 230, a proposed clinical interface output is provided for review. For example, a proposed mapping of content (e.g., a mapping of new interface codes to existing terminology) is automatically provided by a tool based on the comparison to stored or other reference data/terminology. At block 240, review of the output is facilitated. For example, when the proposed output is reviewed, a tester updates and/or verifies the proposal. A table, matrix, or other representation of the proposed mapping can be provided for automated (e.g., software, hardware and/or firmware) and/or manual (e.g., human user) review, for example. A specification is then created as output for testing.

At block 250, the clinical interface mapping specification is loaded into (e.g., implemented in) a clinical system (e.g., a clinical information system). For example, the output provides a proposed clinical interface mapping for testing based on coded terminology and data. At block 260, testing of the clinical interface is facilitated. For example, data can be provided to the clinical interface to test accuracy of the mapping of the data. Usage of the interface mapping by a user can be monitored and evaluated, for example. Testability, via an interface and tool(s), allows a user to rapidly configure and map a large portion of content from a new interface and turn on or activate the interface to begin testing and continue with implementation, for example.

At block 270, the clinical interface is validated and made available for use. For example, one or more new clinical content feeds are mapped to a "standard" clinical application core using the validated specification. At block 280, clinical data is added to the reference repository. Thus, when new clinical feeds are processed, tested, and mapped to the standard core, the clinical data can be added to the reference repository. Output continues to improve over time and increase the robustness of the reference repository, for example.

FIG. 3 illustrates a flow diagram of an example automated mapping process 300 to enable implementation of a new clinical interface. At block 310, new interface content 305 is provided for parsing and analysis. A repository of mapped content 325 is used for comparison and output 315 of analysis results. For example, at block 312, a clinical categorization of an HL7 feed (e.g., lab, orders, microbiology, radiology, etc.) is content. At block 314, messages from the HL7 feed are parsed to identify codes, data, etc. At block 316, a lexical comparison of codes and descriptions is executed. Comparison can include data type and quantitative comparison of data, for example. At block 318, a CDR and terminology are retrieved based on the clinical categorization. The reference CDR includes de-identified, previously mapped clinical content, for example.

At block 320, outputs are generated. For example, at block 322, one or more sets of code systems are generated for import into the clinical system. At block 324, one or more suggested mapping from new interface codes to retrieved terminology are output.

At block 330, configuration for interface testing is conducted. At block 332, one or more new code systems are imported. At block 334, suggested mappings from interface codes to terminology are reviewed. At block 336, the mappings for new content are approved and imported. At block 338, the new set of mapped and de-identified clinical data is loaded for future use. Thus, the reference repository becomes more comprehensive and robust and new interface feeds and associated content are analyzed.

At block 340, the new interface is tested. At block 342, a complete code system load for the given interface is validated. At block 344, the interface is activated and monitored for errors. Additional codes not uncovered by the automated process can be mapped as testing and monitoring continues, for example. At block 346, appropriate and consistent storage of clinical data from the new interface is validated.

FIG. 4 illustrates a flow diagram of an example automated mapping process 400 to enable implementation of a new clinical interface, applying the process 300 of FIG. 3 to a new laboratory interface feed. At block 412, the lab interface feed is provided for parsing and analysis. An example code from the interface feed 412 can include PROTUR Urine Protein where the Value=3+.

At block 416, a lexical match is made with the Urine Protein descriptor. However, in the example there are two Urine Protein descriptors, one with values of neg, 1+, 2+, 3, etc., and another with values of 0, 120, 300, etc. At block 417, a lexical and data match is determined by examining the data values to select an appropriate Urine Protein descriptor (e.g., (X45) with values neg, 1+, 2+, 3+, etc.). At block 418, database content (e.g., code representing the Urine Protein description variants) is retrieved for comparison at blocks 416 and 417.

At block 422, an output file is provided including the code and description (e.g., the PROTUR code and Urine Protein description). At block 424, an output of the lexical and data match is provided.

At block 432, a new lab code system including the code and descriptor (e.g., Code: PROTUR, Description: Urine Protein) are configured for interface testing. At block 434, the lexical and data match output mapping is verified or agreed by an automated and/or manual interface test. At block 436, a new map is created indicating that, for example, the code PROTUR is equivalent to the code X45 corresponding to Urine Protein with values of neg, 1+, 2+, 3+, etc.

At block 442, the new lab code system is tested. At block 444, the mapping is verified (e.g., PROTUR is equivalent to X45). At block 446, the new code is stored in the reference repository (e.g., X45 is stored in the CDR as a mapping for PROTUR).

In certain examples, a new interface mapping can be provided to process incoming data from one or more connected devices for storage in a data repository. For example, a processor can normalize data and/or content of a message received via a data interface or other input by mapping the data and/or other content using the generated interface mapping. The mapping can be customizable based on customer preferences and/or needs using the interface, for example. This normalized data may then be translated and stored in a structured format, model, panel, etc., usable in clinical decision support. For example, based on an identifier identifying messages as being from a Healthcare Information System (HIS) of a Hospital and being an A01 message type, a processor can map and/or extract data from the messages to fields of one or more objects associated with A01 message types where the data can then be saved in a structured format at a data store for current and/or later use. For example, based on an identifier identifying messages as being from a Cardiology Department of a Hospital and being observation messages, the processor can map and/or extract data from the messages and then save and/or route the data in a structured format for current and/or later use (such as to correlate data for a patient, provide data usable to determine treatment option(s) for a diagnosis, generate a clinical form or formlet, etc.).

In an example, a controlled medical vocabulary (CMV) is created for a clinical system and/or clinical application that covers a variety of terms (e.g., everything from problem lists to allergies to drugs). The terminology is transferred to an "inbox" with one or more proposed mappings using SNOMED, ICD9, ICD10, LOINC, Digital Imaging and Communications in Medicine (DICOM), American College of Radiology (ACR) Index of Radiological Diagnoses, American National Standards Institute (ANSI) identifiers, etc., and/or into a visual mapping tool where a user can see those mappings in more of a visual way to help a person developing a CMV.

A CMV is a capability of a computer-based patient record (CPR) system. Other CPR core capabilities include clinical documentation and data capture, clinical display including a clinical dashboard, a clinical workflow, order management including physician order entry, a clinical data repository (CDR), clinical decision support (CDS), privacy support, and interoperability connectivity. A CMV supports medically relevant concepts, terms, codes and relationships.

CMV services can be delivered using a vocabulary server that provides access to a set of CMV functions as a series of application programming interfaces (APIs). This approach makes the CMV accessible to any software component in the CPR or its environment that uses such services. In many cases, a set of terminologies such as SNOMED, ICD-9, ICD-10, and Current Procedural Terminology-Fourth Edition (CPT-4), including cross maps between their respective terms, is included. Using the CMV and vocabulary server, vocabulary services can be provided to subsystems of a core CPR system as well as other subsystems in the CPR environment. The CMV and vocabulary server can provide information concerning a medical term or concept to an executing application and can also accept terminology updates.

Using a CMV, CPR systems can understand and more intelligently process medical information while continuing to store that information in a form (e.g., medical terms) that permits humans to interact with the same data. In an example, a user can enter a query against information in a data warehouse (which has received its data from the CDR) asking to retrieve cases corresponding to certain search terms. If the CMV has been used to classify the information in the data warehouse, then the query should successfully retrieve all relevant cases including cases using equivalent terminology. The CMV can provide a comprehensive answer by using a search algorithm to explore its semantic network, for example.

In an example, limited CMV capabilities exist in a CPR system. For example, CMV capabilities allow mapping terms into canonical terms, generating billing codes, etc. These mappings can be hard-coded into applications, for example. In such environments, a CPR system supports generation of standard code sets such as ICD-9 and CPT-4.

In an example, the CMV exists as an architecturally separate component in the CPR. The CMV can be used to explicitly manage concepts, terms, and relationships, as well as cross-mapping these concepts, terms, and relationships to standardized encoding schemes. Applications such as clinical decision support and clinical workflow can have a significant degree of CMV interaction. An API for a vocabulary server supports the vocabulary needs of the clinical decision support and clinical workflow as well as related applications and/or components. The CMV/vocabulary server combination can support tools to enable terminologies to be updated and to resolve resulting conflicts. Proposed CMV content can be compared to current CMV content, establish semantic consistency in the new content, and track changes made to the CMV.

In an example, a vocabulary server supports interacting vocabulary needs of the CPR environment. The vocabulary server permits users to interactively explore the vocabulary's semantic network, maintain local vocabulary variations, incorporate new content, handle versioning issues, and provide real-time (or substantially real-time) responses to queries for vocabulary services. To support a full spectrum of CPR functions, the CMV provides "decompositional completeness". That is, the CMV contains atomic representations of pre-coordinated terms contained in the CMV. Thus, if the CMV includes a pre-coordinated term or phrase including multiple elements, then the CMV includes primitive terms for each of those elements. The CMV also includes a convention or rule that describes how to use the primitive terms for each of the elements to create a post-coordinated term having the identical semantic content as the pre-coordinated term. A CMV that provides decompositional completeness enables applications, such as medical natural language processing applications, to function properly despite the existence of pre-coordinated terms that differ in form from the specific terms that can be created by a CPR system user (e.g., "myocardial infarction" versus "heart attack"). The CMV can also support the clinical workflow and clinical decision support capabilities of the CPR system. CMV can be used to support evidence-based medicine (EBM) functions such as automated care guideline protocols. The CMV also includes support for manual vocabulary updates and resolution of vocabulary semantic conflicts.

In an example, the CMV and vocabulary server support a full range of real-time vocabulary services, as well as being able to receive automated updates from vocabulary authorities. The CMV supports many industry-standard coding systems. The vocabulary server management system supports automated integrity checking of the CMV's semantic network and can provide automated support for EBM functions. The CMV can be combined with capabilities such as clinical workflow, CDS, EBM, natural language processing, and continuous speech recognition to provide an environment where a variety of clinical input (e.g., typing, speech, menu picks, and external documents) are incorporated into the CPR system's functions. The CMV can work in conjunction with clinical workflow and CDS to help provide knowledge management within the CPR system.

In an example, a mapping between external terminologies and use of text-based analysis to provide additional meaning and presentations of medical codes and terms by supplementing the data with localized clinical content is automated. The example process can include the following: 1) An initial CMV is created by cloning sections of external terminologies based on healthcare data domain (e.g., LOINC for laboratory terminology, CPT for medical procedures, etc.). The structures (e.g., relationships, concepts, and terms) of the standard terminologies are retained where applicable. Mappings between the CMV and publicly available mappings (e.g., ICD-9 to ICD-10, SNOMED to CPT, etc.) are then used to create a web of related data. The web of data includes both direct (e.g., equivalent) and indirect mappings (e.g., is broader than, is narrower than). 2) Rules are created based on the mappings to determine how to handle changes to the source terminology. For example, when a new term is added by a third party organization, then the mapping for sister terms can specify to automatically propagate 'additions' or put them into proposed status for review. 3) In addition to creating a CMV based on standard vocabularies, customer presentations and mappings can also be included. To create such a CMV, a healthcare organization aggregates its clinical content including nursing, physician, and administrative documents, for example. Much of this data is currently collected in an unstructured mechanism via comment and note fields and thus very difficult to maintain in a structured terminology system. 4) This unstructured clinical content is then run through a text analyzer and extraction tool to organize the information based on synonyms, abbreviations, and relevance to existing source terminologies, for example. 5) Source terminologies and medical dictionaries are used to augment the intelligence of the text analyzer. 6) Proposed terms and synonyms are extracted based on linguistic and probabilistic algorithms. Proposals are put into a queue for a terminology engineer to validate and promote to the controlled medical vocabulary, for example. 7) Local synonyms and presentations based on the unstructured data analysis can be automatically put into a proposed queue to be added to the CMV.

In an example, controlled medical terminology services and modeling and management tools are used to provide advanced analytics, real-time decision support, and business intelligence through use of structured, coded data. CMV systems store high quality, computationally comparable, reliable, and reusable data to support such services. Additionally, internal and external interoperability of systems, processes, and data can be provided to reduce costs incurred due to redundant and disparate data definition, storage, and maintenance and to promote national and international interoperability by sharing terminology with the healthcare community at large, for example.

Figure 5:
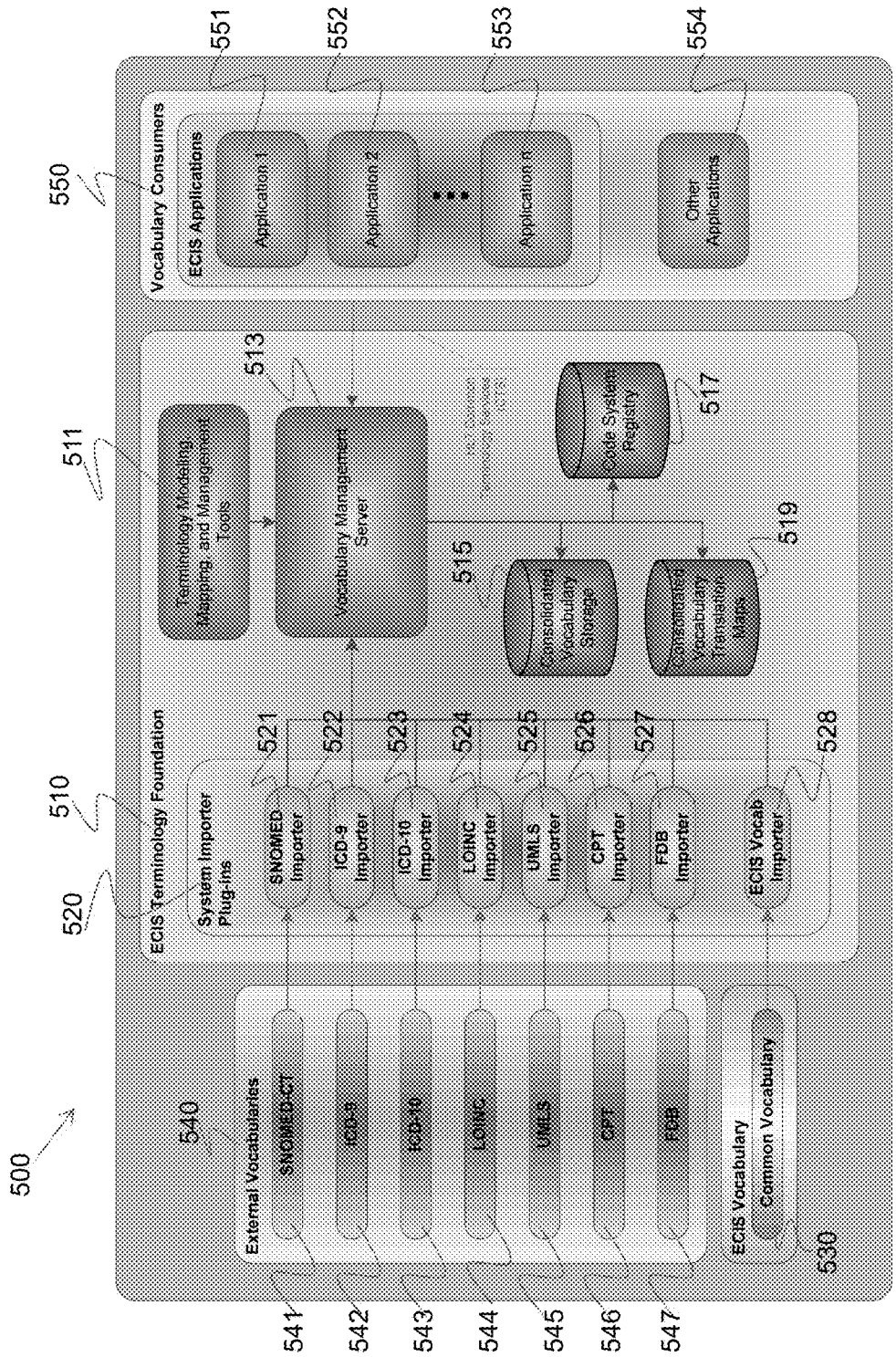
FIG. 5 illustrates an example controlled medical vocabulary (CMV) system.

As shown in FIG. 5, for example, a controlled medical vocabulary (CMV) system 500 includes a terminology foundation subsystem 510, a common vocabulary 530, one or more external vocabularies 540, and one or more vocabulary consumers 550.

The terminology foundation subsystem 510 includes modeling and management tools and common terminology services for code mapping, browsing, and querying services. For example, the terminology foundation subsystem 510 includes terminology modeling, mapping, and management tools 511, a vocabulary management server 513, a consolidated vocabulary storage 515, a code system registry 517, and consolidated vocabulary translation maps 519. The terminology foundation subsystem 510 also includes one or more system importer plug-ins 520. The system importer plug-ins 520 can include one or more of a SNOMED importer 521, an ICD-9 importer 522, an ICD-10 importer 523, a LOINC importer 524, a Unified Medical Language System (UMLS) importer 525, a CPT importer 526, a First Data Bank (FDB) importer 527, and a common vocabulary importer 528.

External vocabulary(ies) 540 can include a SNOMED-CT vocabulary 541, an ICD-9 vocabulary 542, and ICD-10 vocabulary 543, a LOINC vocabulary 544, a UMLS vocabulary 545, a CPT vocabulary 546, an FDB vocabulary 547, etc.

Vocabulary consumer(s) 550 can include one or more applications 551-554. Vocabulary consumers 550 communicate with the terminology foundation subsystem 510 using technology services, such as HL7 Common Technology Services (CTS) 560.

Using the system importer 520 of the terminology foundation subsystem 510, external code systems (e.g., SNOMED, LOINC, CPT, ICD-9, ICD-10, etc.) can be loaded into a consolidated repository. Modeling tools 511 allow informaticists to create, modify, map, and/or manage vocabulary concepts. Data storage and services 513 are used to store and retrieve external code systems 517, translation maps 519, and a controlled medical vocabulary 515. Browsing, code mapping, and runtime services based on the HL7's Common Terminology Services 560 specification support a standards-based controlled medical vocabulary. Versioning, life cycle management, dependency resolution, and packaging services support publishing of terminology across environments.

Concepts from a controlled terminology may not be sufficiently meaningful without a clinical structure to provide context. With a large number of equally correct ways to say the same thing, understanding a desired meaning becomes unreasonably burdensome. Detailed clinical models (DCMs), such as Clinical Element Models (CEMs) developed by Intermountain Healthcare, can be utilized as the basis to model, store, and/or retrieve dynamically changing clinical concepts and information.

A DCM, such as CEM, is a data structure that represents a unit of medical information, including its interrelated components. DCMs enable content-driven systems development so that healthcare delivery can be documented consistently, measured reliably, and improved continuously over time and across patients, providers, care settings, and applications.

Figure 6:
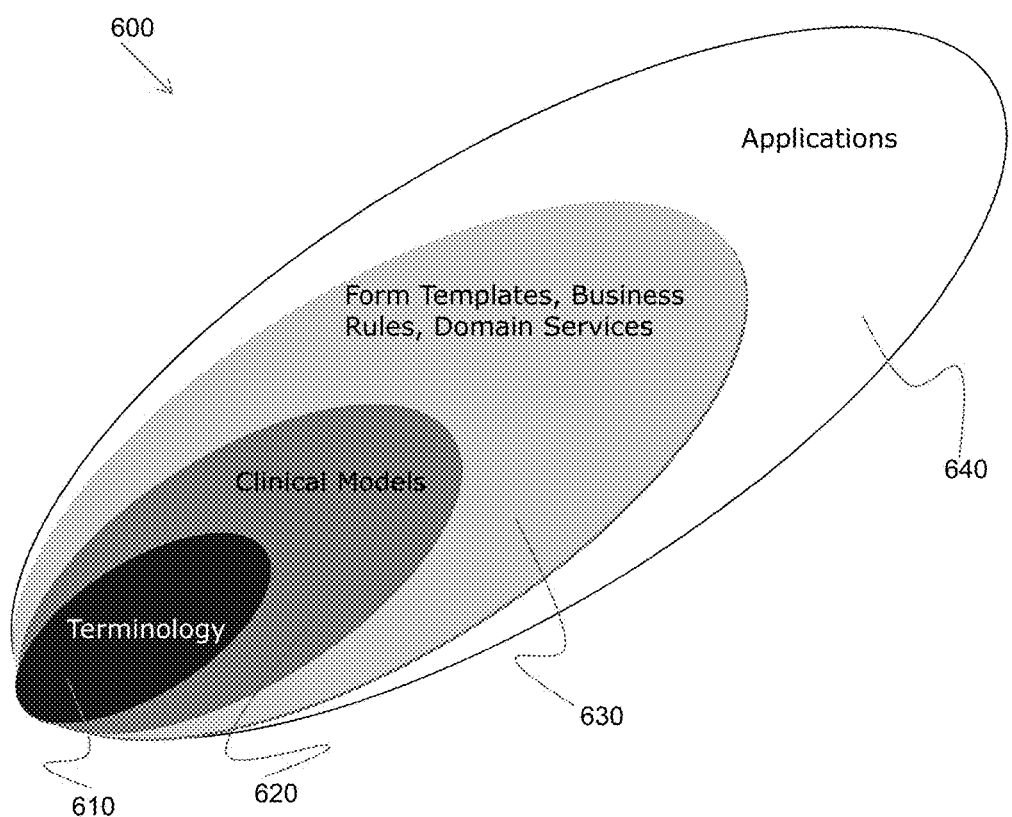
FIG. 6 illustrates an example coded, controlled medical vocabulary that can serve as a basis for understanding clinical data.

A controlled medical vocabulary and clinical models form the basis for a content driven system that supports dynamic data, workflows, and/or decision support. As illustrated, for example, in FIG. 6, a terminology 610 provides a coded, controlled medical vocabulary that can serve as a basis for understanding clinical data. One or more clinical models 620 provide detailed clinical models representing information models bound to the terminology 610. One or more form templates, business rules, and/or domain services 630 provide reusable elements that add context regarding how an application would utilize content. The form templates, business rules, and/or domain services 630 are consumers of the clinical models 620 and terminology 610. One or more applications 640 provide content-driven applications whose behavior is driven by dynamic templates and rules based on the form templates, rules, and/or services 630, clinical models 620, and terminology 610.

Figure 7:
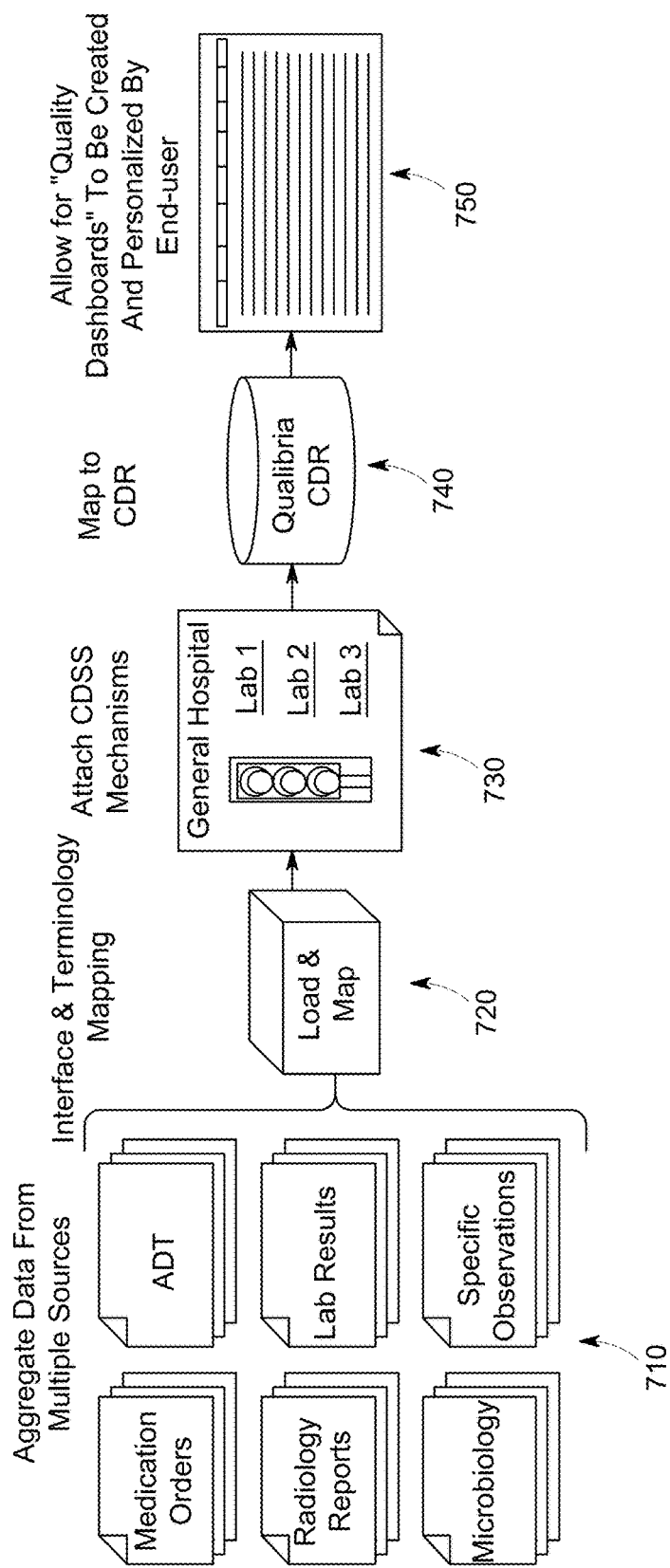
FIG. 7 illustrates an example clinical knowledge system providing an aggregation of data from multiple sources.

In certain examples, a clinical knowledge platform aggregates data from one or more sources/systems from the same and/or different manufacturer and/or provider. For example, as long as there is an HL7 or Web Services feed, the clinical knowledge platform can utilize the data from an existing solution. Existing information technology (IT) solution(s) continue to operate as they always have, and an organization can continue to use these solutions separate from the clinical knowledge platform if they so desire. However, the clinical knowledge platform and associated application(s) and/or workflow(s) can help to put organizations in greater control of their data by aggregating as much data from disparate IT solutions as possible. FIG. 7 illustrates an example clinical knowledge system 700 providing an aggregation 710 of data from multiple sources. Aggregated data may include, for example, medication orders, radiology reports, microbiology, admit/discharge/transfer (ADT) message, lab results, specific observations, electronic medical record (EMR) data, etc. An interface feed mapping interface can be used to provide information for aggregation and processing, for example.

As the different data sources are pulled into a central data repository, content standardization occurs. It is this "standardization" that enables content from different IT sources to be used together. For example, as shown in FIG. 7, an interface 720 provides terminology mapping and standardization to the aggregated data.

After the content is standardized, clinical decision support mechanisms can be tied to the content (as illustrated, for example, by the clinical decision support 730 of the system 700 of FIG. 7). The data and associated clinical decision support are then stored in a clinical data repository (CDR), such as CDR 740 of the example system 700. By combining the aggregated and standardized data with clinical decision support rules and alerts, the clinical knowledge platform may provide end-users with an understanding of important elements to which they should pay attention (and take action on) within the larger set of data they are considering when caring for a patient.

Combined data and clinical decision support mechanisms create valuable content that, when arranged properly, may be used to improve the quality of care provided. Organizations can elect to use the application(s) that are provided as a part of the example clinical knowledge platform and/or may choose to build their own clinical application(s) on the platform. The open architecture nature of the platform empowers organizations to build their own vision, rather than base their vision on the static/hard coded nature of traditional IT solutions.

In certain examples, "Quality Dashboards" created via an example application display data via columns and rows in addition to individual patient "inspector" views. For example, the system 700 shown in FIG. 7 provides one or more quality dashboards 750 to be created and personalized by an end user. The flexible nature of this dashboard application empowers organizations to create dashboards of the aggregated data based on their needs at a given period of time. The organization may determine what data elements they would like to include on each dashboard and, without significant IT resources, create a dashboard that reflects their vision. In addition, organizations can determine where on the dashboard they would like the information to be displayed and further adjust the view of the content via features such as "bolding" font, etc. When data is added to each dashboard, clinical decision support mechanisms attached to this data are displayed on the dashboard as well. For example, content related to treating a patient based on a particular use case may be included on a quality dashboard, along with alerts and notifications to indicate to end-users when desired outcomes are varying from defined clinical standards. Thus, organizations can create dashboards based on their own idea of "best practice" care for a given disease state.

In certain examples, since combined content and best practices have been standardized, content from one organization using the clinical knowledge platform may be easily shared with other organizations utilizing the platform. In addition, because the content within platform-related applications is standardized in the same manner, upgrades to the example platform can occur efficiently across organizations. That represents a dramatic change from prior IT solutions which require unique IT upgrades because they are usually uniquely customized to each organization in which they are installed.

Figure 8:
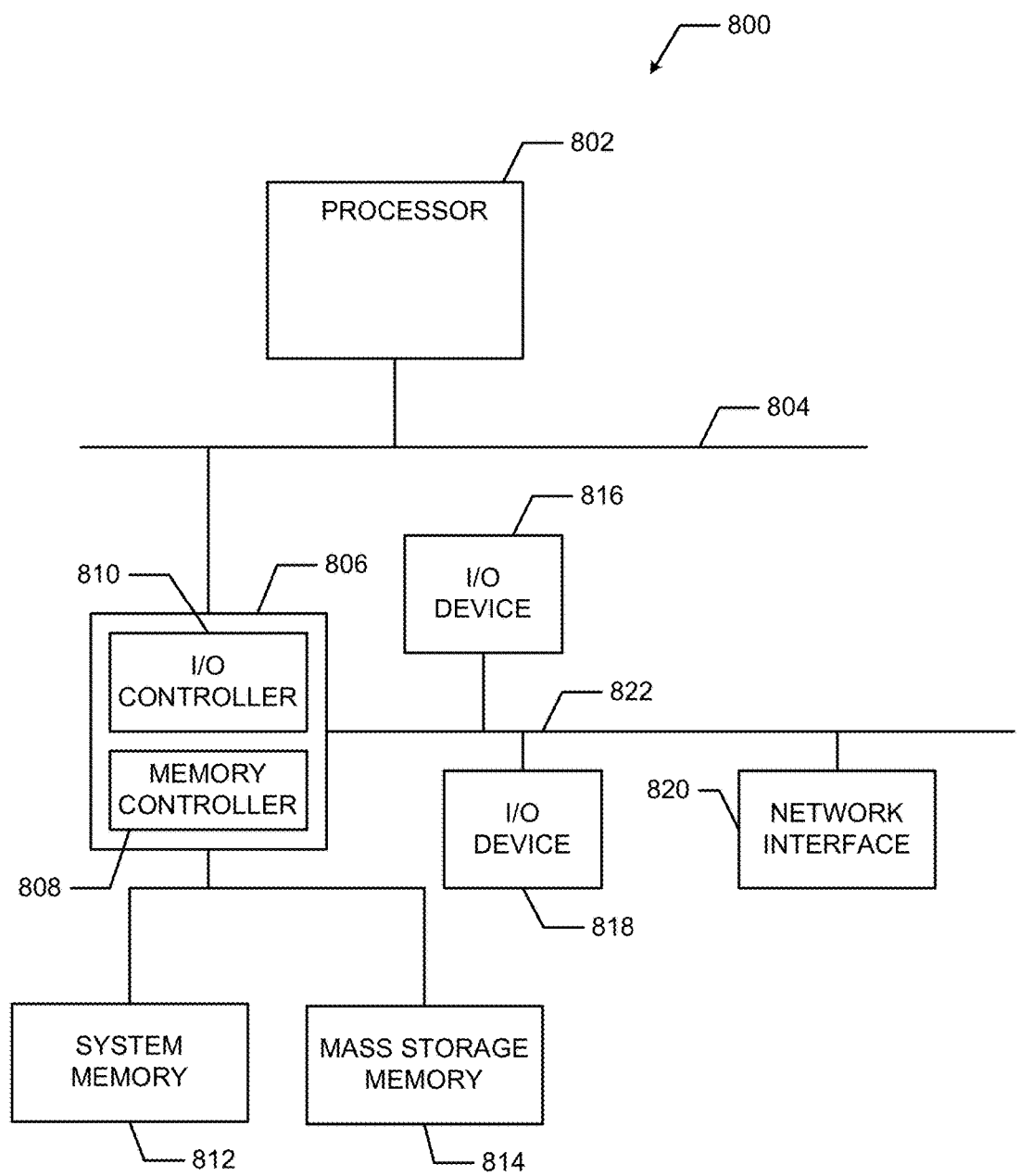
FIG. 8 is a block diagram of an example processor system that may be used to implement systems, apparatus, and methods described herein.

FIG. 8 is a block diagram of an example processor system 810 that can be used to implement systems, apparatus, and methods described herein. As shown in FIG. 8, the processor system 810 includes a processor 812 that is coupled to an interconnection bus 814. The processor 812 can be any suitable processor, processing unit, or microprocessor, for example. Although not shown in FIG. 8, the system 810 can be a multi-processor system and, thus, can include one or more additional processors that are identical or similar to the processor 812 and that are communicatively coupled to the interconnection bus 814. For example, "cloud" and/or "grid" based computing can be employed for three dimensional processing using Euclidian vectors and linear algebra. In certain examples, a Bayesian algorithm can be used in an evolving model combining multiple executions of multiple algorithms. As certain mappings are resolved, a probability associated with other remaining mappings changes.

The processor 812 of FIG. 8 is coupled to a chipset 818, which includes a memory controller 820 and an input/output ("I/O") controller 822. As is well known, a chipset typically provides I/O and memory management functions as well as a plurality of general purpose and/or special purpose registers, timers, etc. that are accessible or used by one or more processors coupled to the chipset 818. The memory controller 820 performs functions that enable the processor 812 (or processors if there are multiple processors) to access a system memory 824 and a mass storage memory 825.

The system memory 824 can include any desired type of volatile and/or non-volatile memory such as, for example, static random access memory (SRAM), dynamic random access memory (DRAM), flash memory, read-only memory (ROM), etc. The mass storage memory 825 can include any desired type of mass storage device including hard disk drives, optical drives, tape storage devices, etc.

The I/O controller 822 performs functions that enable the processor 812 to communicate with peripheral input/output ("I/O") devices 826 and 828 and a network interface 830 via an I/O bus 832. The I/O devices 826 and 828 can be any desired type of I/O device such as, for example, a keyboard, a video display or monitor, a mouse, etc. The network interface 830 can be, for example, an Ethernet device, an asynchronous transfer mode ("ATM") device, an 802.11 device, a DSL modem, a cable modem, a cellular modem, etc., that enables the processor system 810 to communicate with another processor system.

While the memory controller 820 and the I/O controller 822 are depicted in FIG. 8 as separate blocks within the chipset 818, the functions performed by these blocks can be integrated within a single semiconductor circuit or can be implemented using two or more separate integrated circuits.

Certain embodiments contemplate methods, systems and computer program products on any machine-readable media to implement functionality described above. Certain embodiments can be implemented using an existing computer processor, or by a special purpose computer processor incorporated for this or another purpose or by a hardwired and/or firmware system, for example.

Some or all of the system, apparatus, and/or article of manufacture components described above, or parts thereof, can be implemented using instructions, code, and/or other software and/or firmware, etc. stored on a machine accessible or readable medium and executable by, for example, a processor system (e.g., the example processor system 810 of FIG. 8). When any of the appended claims are read to cover a purely software and/or firmware implementation, at least one of the components is hereby expressly defined to include a tangible medium such as a memory, DVD, CD, Blu-ray disc, etc. storing the software and/or firmware.

Thus, certain examples described herein facilitate use of reduced manpower associated with manually matching terms between two or more code schemes, as well as helping to provide faster interoperability configuration. Certain examples provide more reliable concept matching by computer-generated determination of match probabilities augmented by user confirmation. Certain examples provide both alphanumeric and graphical representations of likely concept matches for both automated and manual review and confirmation of a probable concept match. Certain examples provide technical effects of advanced analytics, real-time decision support, and business intelligence through use of structured, coded data. Certain examples help reduce costs incurred due to redundant and disparate data definition, storage, and maintenance and help promote national and international interoperability by sharing terminology with the healthcare community at large.

Certain embodiments contemplate methods, systems and computer program products on any machine-readable media to implement functionality described above. Certain embodiments can be implemented using an existing computer processor, or by a special purpose computer processor incorporated for this or another purpose or by a hardwired and/or firmware system, for example.

Certain embodiments include computer-readable media for carrying or having computer-executable instructions or data structures stored thereon. Such computer-readable media can be any available media that can be accessed by a general purpose or special purpose computer or other machine with a processor. By way of example, such computer-readable media can include RAM, ROM, PROM, EPROM, EEPROM, Flash, CD-ROM, DVD, Blu-ray or other optical disk storage, magnetic disk storage or other magnetic storage devices, or any other medium which can be used to carry or store desired program code in the form of computer-executable instructions or data structures and which can be accessed by a general purpose or special purpose computer or other machine with a processor. Combinations of the above are also included within the scope of computer-readable media. Computer-executable instructions include, for example, instructions and data which cause a general purpose computer, special purpose computer, or special purpose processing machines to perform a certain function or group of functions.

Generally, computer-executable instructions include routines, programs, objects, components, data structures, etc., that perform particular tasks or implement particular abstract data types. Computer-executable instructions, associated data structures, and program modules represent examples of program code for executing steps of certain methods and systems disclosed herein. The particular sequence of such executable instructions or associated data structures represent examples of corresponding acts for implementing the functions described in such steps.

Embodiments of the present invention can be practiced in a networked environment using logical connections to one or more remote computers having processors. Logical connections can include a local area network (LAN) and a wide area network (WAN) that are presented here by way of example and not limitation. Such networking environments are commonplace in office-wide or enterprise-wide computer networks, intranets and the Internet and can use a wide variety of different communication protocols. Those skilled in the art will appreciate that such network computing environments will typically encompass many types of computer system configurations, including personal computers, hand-held devices, multi-processor systems, microprocessor-based or programmable consumer electronics, network PCs, minicomputers, mainframe computers, and the like. Embodiments of the invention can also be practiced in distributed computing environments where tasks are performed by local and remote processing devices that are linked (either by hardwired links, wireless links, or by a combination of hardwired or wireless links) through a communications network. In a distributed computing environment, program modules can be located in both local and remote memory storage devices.

While the invention has been described with reference to certain embodiments, it will be understood by those skilled in the art that various changes can be made and equivalents can be substituted without departing from the scope of the invention. In addition, many modifications can be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A computer-implemented method of mapping a clinical interface message feed to reference clinical data and coded terminology, said method comprising:
    receiving, at an interface analyzer including a processor, a clinical message feed including content;
    automatically comparing, using the processor, a detailed clinical model, and a controlled medical vocabulary, the content from the clinical message feed to a reference including de-identified previously mapped clinical content to match and map the content to at least one of reference clinical data and coded terminology included in the reference without user input, the comparing to match and map the content forming a proposed interface mapping output, the proposed interface mapping output built using a tool provided by the processor to generate a representation and specification of an interface for device communication;
    providing the proposed interface mapping output for review via the interface analyzer;
    facilitating testing, via the interface analyzer, of the proposed interface mapping output in conjunction with a clinical system by activating the proposed interface mapping to process data and monitoring the proposed interface mapping output for errors and, when an error occurs, continuing testing of the proposed interface mapping and mapping additional codes not identified in the automated comparing, the testing of the proposed interface mapping to validate the proposed interface mapping output based on data from the clinical system and the at least one of reference clinical data and coded terminology from the reference, the testing of the proposed interface mapping to continue until no errors are identified when processing the data;
    releasing, when validated, the proposed interface mapping output as a clinical interface incorporated into the clinical system by configuring a processor in the clinical system to enable a connected device to communicate with the clinical system, the clinical interface providing a mapping for incoming messages from the connected device at the clinical system; and
    updating the reference based on the content from the clinical message feed and the testing of the proposed interface mapping output.

2. The method of claim 1, wherein comparing further comprises parsing the content of the clinical message feed according to at least one of a lexicon and a format.

3. The method of claim 1, wherein the clinical message feed comprises a Health Level Seven (HL7) message feed.

4. The method of claim 1, further comprising validating the proposed interface mapping output based on storage of clinical data via the proposed interface mapping output.

5. The method of claim 1, wherein the reference comprises a clinical data repository.

6. The method of claim 1, wherein the reference comprises a predefined clinical terminology.

7. A clinical interface feed analysis system comprising:
    an interface analyzer to:
    receive a clinical message feed including content;
    automatically compare, using a detailed clinical model, and a controlled medical vocabulary, the content from the clinical message feed to a reference including de-identified previously mapped clinical content to match and map the content to at least one of reference clinical data and coded terminology included in the reference without user input, the comparing to match and map the content forming a proposed interface mapping output, the proposed interface mapping output built using a tool provided by the interface analyzer to generate a representation and specification of an interface for device communication; and
    provide the proposed interface mapping output for review; and
    a tester to facilitate testing of the proposed interface mapping output in conjunction with a clinical system by activating the proposed interface mapping to process data and monitoring the proposed interface mapping output for errors and, when an error occurs, continuing testing of the proposed interface mapping and mapping additional codes not identified in the automated comparing, the testing of the proposed interface mapping to validate the proposed interface mapping output based on data from the clinical system and the at least one of reference clinical data and coded terminology from the reference, the testing of the proposed interface mapping to continue until no errors are identified when processing the data, the tester to release, when validated, the proposed interface mapping output as a clinical interface incorporated into the clinical system by configuring a processor in the clinical system to enable a connected device to communicate with the clinical system, the clinical interface providing a mapping for incoming messages from the connected device at the clinical system,
    wherein the system is to update the reference based on the content from the clinical message feed and the testing of the proposed interface mapping output.

8. The system of claim 7, wherein the interface analyzer comprises a parser to parse the content of the clinical message feed according to at least one of a lexicon and a format and a matcher to match and map the content.

9. The system of claim 7, wherein the clinical message feed comprises a Health Level Seven (HL7) message feed.

10. The system of claim 7, wherein the tester is to validate the proposed interface mapping output based on storage of clinical data via the proposed interface mapping output.

11. The system of claim 7, wherein the reference comprises a clinical data repository.

12. The system of claim 7, wherein the reference comprises a predefined clinical terminology.

13. A tangible computer readable storage medium including executable program instructions which, when executed by a computer processor, cause the computer to implement a clinical interface feed analysis system comprising:
   an interface analyzer to:
      receive a clinical message feed including content;
      automatically compare, using a detailed clinical model, and a controlled medical vocabulary, the content from the clinical message feed to a reference including de-identified previously mapped clinical content to match and map the content to at least one of reference clinical data and coded terminology included in the reference without user input, the comparing to match and map the content forming a proposed interface mapping output, the proposed interface mapping output built using a tool provided by the interface analyzer to generate a representation and specification of an interface for device communication; and
      provide the proposed interface mapping output for review; and
   a tester to facilitate testing of the proposed interface mapping output in conjunction with a clinical system by activating the proposed interface mapping to process data and monitoring the proposed interface mapping output for errors and, when an error occurs, continuing testing of the proposed interface mapping and mapping additional codes not identified in the automated comparing, the testing of the proposed interface mapping to validate the proposed interface mapping output based on data from the clinical system and the at least one of reference clinical data and coded terminology from the reference, the testing of the proposed interface mapping to continue until no errors are identified when processing the data, the tester to release, when validated, the proposed interface mapping output as a clinical interface incorporated into the clinical system by configuring a processor in the clinical system to enable a connected device to communicate with the clinical system, the clinical interface providing a mapping for incoming messages from the connected device at the clinical system,
   wherein the system is to update the reference based on the content from the clinical message feed and the testing of the proposed interface mapping output.

14. The computer readable medium of claim 13, wherein the interface analyzer comprises a parser to parse the content of the clinical message feed according to at least one of a lexicon and a format and a matcher to match and map the content.

15. The computer readable medium of claim 13, wherein the tester is to validate the proposed interface mapping output based on storage of clinical data via the proposed interface mapping output.

16. The computer readable medium of claim 13, wherein the reference comprises a clinical data repository.

17. The computer readable medium of claim 13, wherein the reference comprises a predefined clinical terminology.

* * * * *